(12) United States Patent
Stoutenburgh et al.

(10) Patent No.: US 9,492,126 B2
(45) Date of Patent: Nov. 15, 2016

(54) RADIOLOGICAL IMAGING SYSTEM

(71) Applicant: Epica International, Inc., San Clemente, CA (US)

(72) Inventors: Gregory William Stoutenburgh, San Clemente, CA (US); Damiano Fortuna, Rignano Sull'Arno (IT); Luca Ferretti, Pisa (IT)

(73) Assignee: Epica International, Inc., San Clemente, CA (US)

( * ) Notice: Subject to any disclaimer, the term of this patent is extended or adjusted under 35 U.S.C. 154(b) by 108 days.

(21) Appl. No.: 14/603,917

(22) Filed: Jan. 23, 2015

(65) Prior Publication Data

US 2015/0208990 A1    Jul. 30, 2015

Related U.S. Application Data

(60) Provisional application No. 61/932,034, filed on Jan. 27, 2014, provisional application No. 61/944,956, filed on Feb. 26, 2014.

(51) Int. Cl.
| | |
|---|---|
| *A61B 6/04* | (2006.01) |
| *A61B 6/00* | (2006.01) |
| *A61G 7/10* | (2006.01) |
| *A61B 6/03* | (2006.01) |

(52) U.S. Cl.
CPC ............. *A61B 6/0407* (2013.01); *A61B 6/032* (2013.01); *A61B 6/0442* (2013.01); *A61B 6/0492* (2013.01)

(58) Field of Classification Search
USPC ....... 378/204, 209–210; 250/370.09, 455.11, 250/526
See application file for complete search history.

(56) References Cited

U.S. PATENT DOCUMENTS

| | | | |
|---|---|---|---|
| 2,113,286 A | 4/1938 | White | |
| 7,488,946 B2 * | 2/2009 | Hennessy | ............ A61B 6/4233 250/370.09 |
| 2010/0050339 A1 | 3/2010 | Beard et al. | |
| 2012/0104276 A1 | 5/2012 | Miller et al. | |
| 2012/0253177 A1 * | 10/2012 | Drobnik | ................. A61B 5/055 600/411 |
| 2015/0208991 A1 * | 7/2015 | Stoutenburgh | ....... A61B 6/0407 378/62 |

* cited by examiner

*Primary Examiner* — Bernard Souw
(74) *Attorney, Agent, or Firm* — Steptoe & Johnson LLP

(57) ABSTRACT

A radiological imaging system for obtaining images of at least a portion of the internal anatomy of a patient is disclosed. According to one embodiment, the radiological imaging system includes a bed extending along a main direction and including a support surface substantially concave to permit the bed to contain at least a portion of the patient. The radiological imaging system further includes a source suitable to emit radiation, and a detector suitable to receive the radiation. Also, the radiological imaging system may include a load-bearing structure suitable to support the bed, the source and the detector.

27 Claims, 3 Drawing Sheets

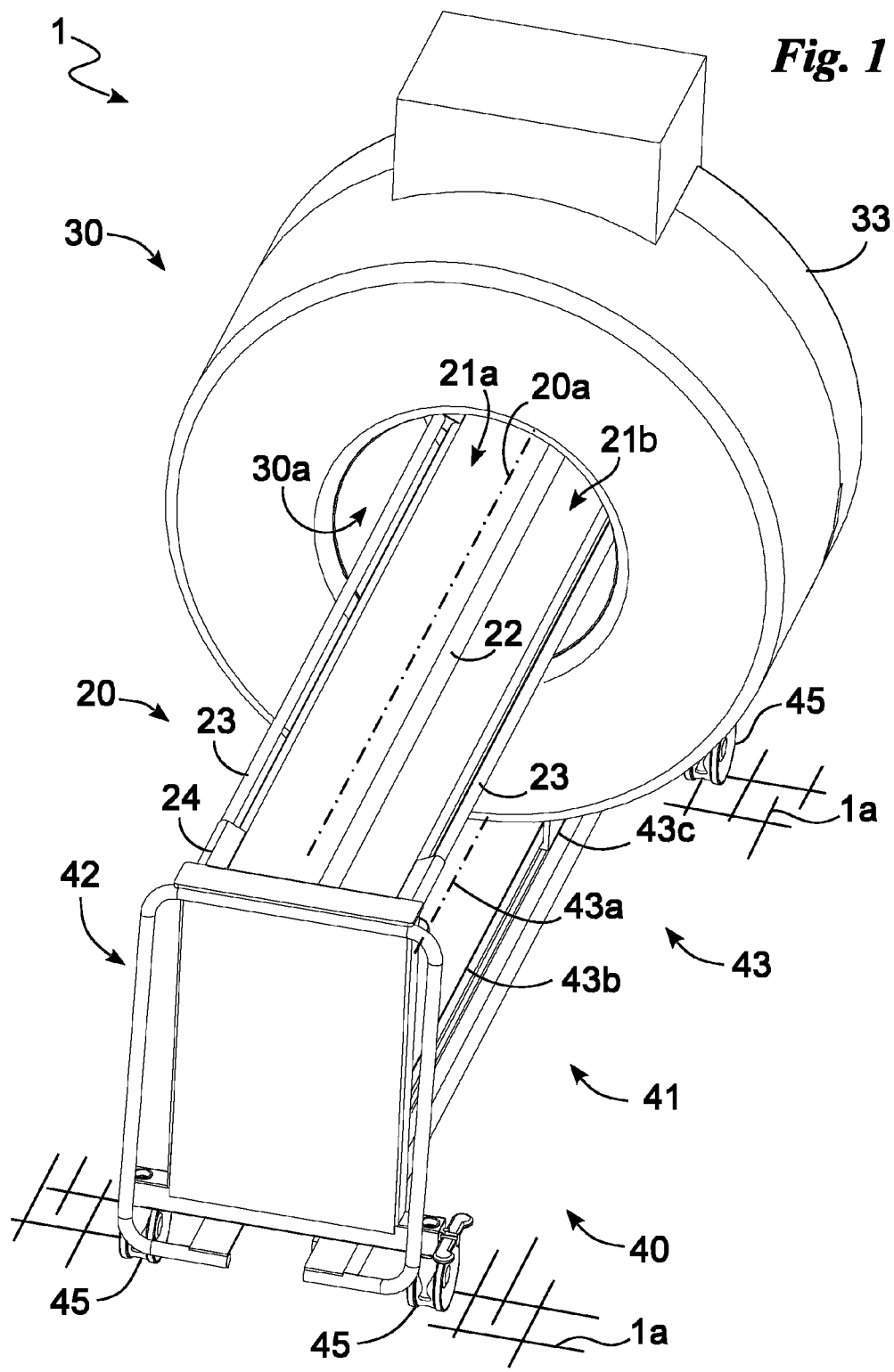

RADIOLOGICAL IMAGING SYSTEM

CROSS-REFERENCE TO RELATED APPLICATIONS

The present application claims the benefit of and priority to U.S. Provisional Patent Application Ser. Nos. 61/932,034 filed on Jan. 27, 2014 and 61/944,956 filed on Feb. 26, 2014, which are hereby incorporated by reference.

This application is related to co-pending U.S. patent application Ser. No. 14/603,951, filed Jan. 23, 2015, entitled RADIOLOGICAL IMAGING SYSTEM WITH ADJUSTABLE BED, which is hereby incorporated by reference in their entirety.

FIELD

The present disclosure relates in general to the field of a radiological imaging system, and in particular, to a system and method for providing a radiological imaging system including a concave bed.

BACKGROUND

Radiological imaging devices currently available on the market have a standard structure including a flat bed on which a patient is placed in order to perform image scanning of the patient. To keep the patient still during the image scanning and thereby ensure the expected performance of the radiological imaging procedure, the bed is typically fitted with straps to restrain the patient. However, the straps may prevent the passage of the X-rays and thereby the correct visualization of the portions adjacent to the straps.

For this reason, in some imaging procedures, the straps covering a portion of the area of interest are practically unusable, and the patient may be required to stay still or held by the operator, who is therefore exposed to the X-rays. Additionally, the radiological imaging device may require a specific detector for each analysis and can perform only one type of analysis at a time.

As a result, in the case in which a patient needs to undergo several analyses, the patient needs to be taken from the radiological imaging device, placed on a bed, moved, picked up again and then laid on a second radiological imaging device. Such maneuvers often entail problems for the patient and the procedure, and therefore need to be performed with particular care and expertise. Consequently, the length of time needed to perform the aforementioned maneuvers increases.

SUMMARY

Existing limitations associated with the foregoing, as well as other limitations, can be overcome by a system and method including a bed and a radiological imaging device, and a bed for use with a radiological imaging device. Although the bed is described in relation to a radiological imaging device, the bed may be used with other devices or simply to transport a patient.

Briefly, and in general terms, the present disclosure is directed to various embodiments of a radiological imaging system. The radiological imaging system permits the patient to be moved simply and quickly, and reduces risks to the patient. According to one embodiment, the radiological imaging system includes a bed extending along a main direction and having a support surface for the patient. The support surface maybe a substantially concave to permit the bed to contain at least a portion of the patient. The radiological imaging system also includes a source suitable to emit radiation and at least one detector suitable to receive the radiation and to be positioned substantially on an opposite side to the source in relation to the bed.

In one embodiment, the bed includes at least two separate bodies defining a portion of the support surface. The two separate bodies may be reciprocally inclined by an angle of aperture ($\alpha$) substantially between 180° and 45°. In another embodiment, angle of aperture ($\alpha$) is between 150° and 90°. It has also been contemplated that the angle of aperture ($\alpha$) may be between 180° and 20°.

In certain embodiments, the bed further includes a hinge suitable to retain the separate bodies allowing the separate bodies to rotate about an axis of rotation. The hinge may be an elastic hinge. The axis of rotation is substantially parallel to the main direction. The bed may be made of a radio-transparent material, for example, carbon fiber or any other suitable radio-transparent material.

In another embodiment, the radiological imaging system includes a load-bearing structure to support the bed, the source and the detector. The radiological imaging system may further include at least one retaining apparatus suitable to removably fix the load-bearing structure to the bed. This allows the bed to be secured to the load-bearing structure during a procedure and then removed from the load-bearing structure after the procedure. After removing the bed from the load-bearing structure, the patient may be transported in the bed to another location. In one embodiment, the at least one retaining apparatus is suitable to fix the load-bearing structure to the bed using a snap-fit attachment. Other types of retaining apparatus may also be used, including Velcro, ties, hooks, screws, removable bolts, or the like.

The present disclosure also is directed to a method of obtaining radiological images of a patient. In one embodiment, the method includes placing the patient on a concave support surface of a bed so the bed contains at least a portion of the patient. In one embodiment, the bed includes at least two separate bodies defining a portion of the support surface. The two separate bodies may be reciprocally inclined by an angle of aperture ($\alpha$) substantially between 180° and 45°. In another embodiment, the angle of aperture ($\alpha$) is between 150° and 90°. The bed may include a hinge, including an elastic hinge, suitable to retain the separate bodies allowing the separate bodies to rotate about an axis of rotation. The bed may be made of a radio-transparent material, for example, carbon fiber or any other suitable radio-transparent material.

In one embodiment, the method also includes emitting radiation from a source to a portion of the patient, and receiving the radiation using at least one detector. The at least one detector may be positioned substantially on an opposite side to the source in relation to the bed.

In certain embodiments, the method includes attaching the bed to the radiological imaging system with at least one retaining apparatus. This allows the bed to be secured to the radiological imaging system during a procedure and then removed after the procedure. After removing the bed from the radiological imaging system, the patient may be transported in the bed to another location. In one embodiment, the at least one retaining apparatus is suitable to fix the load-bearing structure to the bed using a snap-fit attachment. Other types of retaining apparatus may also be used, including Velcro, ties, hooks, screws, removable bolts, or the like.

The present disclosure also is directed to a bed for adjusting a position of a patient. In one embodiment, the bed includes a support surface for the patient and at least two separate bodies. The support surface is substantially concave to permit the bed to contain at least a portion of the patient. The bed may further include a hinge, such as an elastic hinge or the like. The two separate bodies define a portion of the support surface and are reciprocally inclined by an angle of aperture ($\alpha$). The angle of aperture ($\alpha$) may be substantially between 180° and 45°. In another embodiment, the angle of aperture ($\alpha$) is between 150° and 90°. The hinge is suitable to retain the separate bodies allowing the separate bodies to rotate about an axis of rotation that is substantially parallel to a main direction of the bed.

Other features and advantages will become apparent from the following detailed description, taken in conjunction with the accompanying drawings, which illustrate by way of example, the features of the various embodiments.

BRIEF DESCRIPTION OF THE DRAWINGS

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 1 shows an exemplary radiological imaging system, according to one embodiment;

DETAILED DESCRIPTION

Figure 2A:
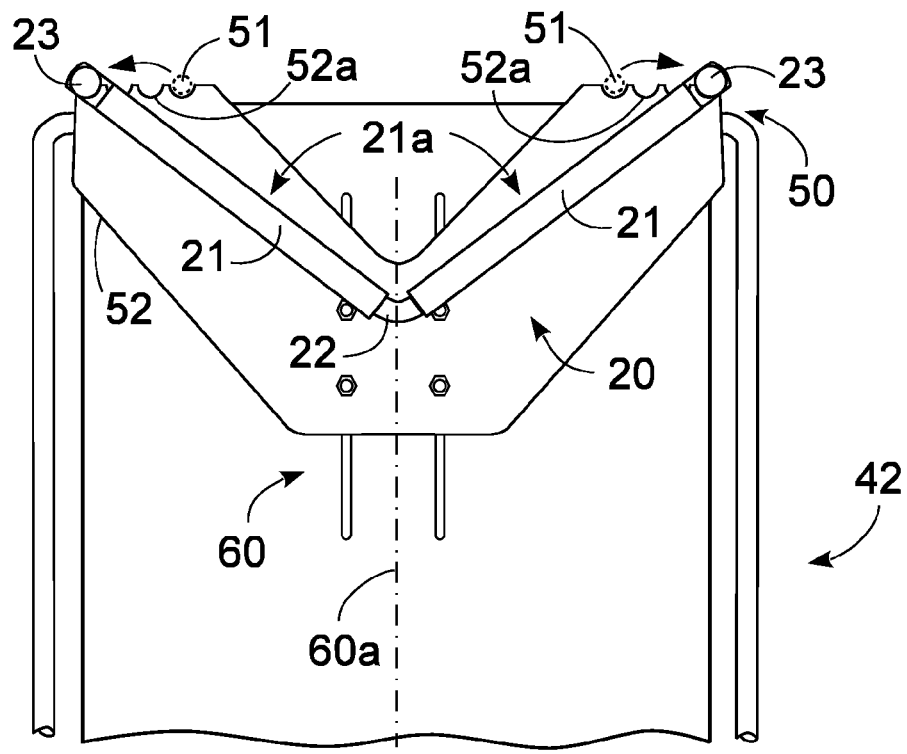
FIGS. 2a and 2b show a cross-section of part of the radiological imaging system of FIG. 1.

Each of the features and teachings disclosed herein can be utilized separately or in conjunction with other features and teachings to provide a radiological imaging system with a bed. Representative examples utilizing many of these additional features and teachings, both separately and in combination are described in further detail with reference to the attached figures. This detailed description is merely intended to teach a person of skill in the art further details for practicing aspects of the present teachings and is not intended to limit the scope of the claims. Therefore, combinations of features disclosed above in the detailed description may not be necessary to practice the teachings in the broadest sense, and are instead taught merely to describe particularly representative examples of the present teachings.

In the description below, for purposes of explanation only, specific nomenclature is set forth to provide a thorough understanding of the present disclosure. However, it will be apparent to one skilled in the art that these specific details are not required to practice the teachings of the present disclosure.

Some portions of the detailed descriptions herein are presented in terms of processes and symbolic representations of operations on data bits within a computer memory. These process descriptions and representations are the means used by those skilled in the data processing arts to most effectively convey the substance of their work to others skilled in the art. A process is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. The steps are not intended to be performed in a specific sequential manner unless specifically designated as such.

The methods or processes presented herein are not inherently related to any particular computer or other apparatus. Various general-purpose systems, computer servers, or personal computers may be used with programs in accordance with the teachings herein, or it may prove convenient to construct a more specialized apparatus to perform the method steps. The structure for a variety of these systems will appear from the description below. It will be appreciated that a variety of programming languages may be used to implement the teachings of the disclosure as described herein.

Moreover, the various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure. It is also expressly noted that the dimensions and the shapes of the components shown in the figures are designed to help to understand how the present teachings are practiced, but not intended to limit the dimensions and the shapes shown in the examples.

With reference to FIGS. 1-4, reference numeral 1 denotes a radiological imaging system. The radiological imaging system 1 is useful in both the medical and veterinary applications for performing radiological imaging of at least one portion of the internal anatomy of a patient. In particular, the radiological imaging system 1 is suitable for performing X-rays, CT scans, fluoroscopy and other radiological imaging examinations.

In one embodiment, the imaging system 1 includes a control unit suitable to control the radiological imaging system 1. The system also includes a bed 20 extends along a main direction 20a and having a support surface for the patient. A gantry 30 suitable to perform the radiological imaging of at least one portion of the patient and defining an analysis zone 30a suitable to house at least a portion of the bed 20. For example, the gantry may have a circular shape as shown in FIG. 1, which is suitable to house at least one portion of the bed 20. Further, the radiological imaging system shown in the embodiment of FIG. 1 includes a load-bearing structure 40 suitable to support the bed 20 and the gantry 30.

Figure 4:
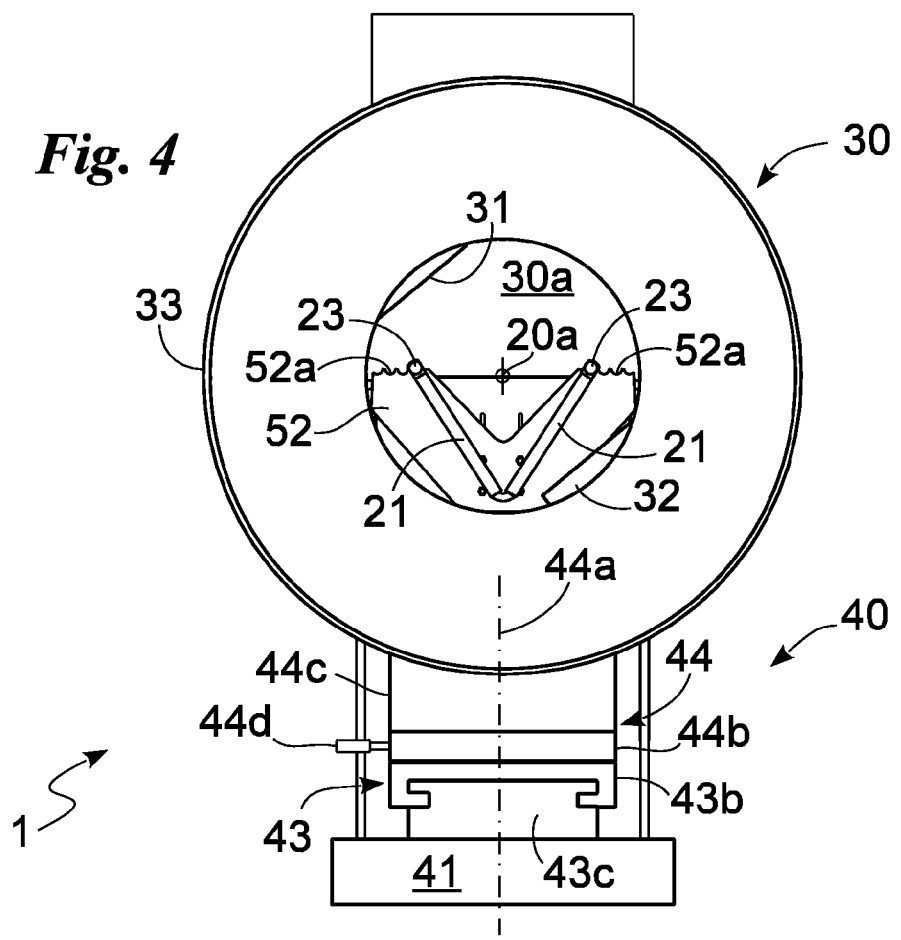
FIG. 4 shows a cross-section of the radiological imaging system of FIG. 1.

As best shown in FIG. 4, the gantry 30 contains various components for performing the radiological scan. Examples of the components contained in the gantry 30 include, but are not limited to the following. A source 31 suitable to emit radiation, for example X-rays. The gantry may also include at least one detector 32 suitable to receive the radiation emitted by the source 31 and suitable to be positioned substantially on the opposite side of the bed 20 to the source as shown in the embodiment of FIG. 4. Further, the gantry may include a housing 33 suitable to contain at least partially the aforementioned components, and the housing may contain addition components as needed. In particular, the detector 32 is suitable to detect the radiation (e.g., X-ray) that has traversed the patient's body during a scan. In one embodiment, the detector 32 may include a sensing element such as a flat panel and/or a linear sensor.

As shown in the examples of FIG. 1, the load-bearing structure 40 includes a base 41 suitable to come into contact with the floor 1a and to support the gantry 30. Also in this example is at least one column 42 suitable to support the bed 20 in a raised position from the floor 1a. As shown in FIG. 1 there may be two columns 42 to support the bed. However, additional columns may be included to support the weight of the bed and the patient. In one embodiment, the structure includes a translating component 43 suitable to move the gantry 30 in a sliding direction 43a substantially parallel to the main direction 20a. As shown in the example of FIG. 4, the structure may also include a rotation device 44 suitable to rotate the gantry 30 about an axis of rotation 44a that is substantially perpendicular to the main direction 20a and, specifically, substantially perpendicular to the floor 1a. In addition, wheels 45 (FIG. 1), which may be pivoting wheels, suitable to roll on the floor 1a when moving the radiological imaging system 1.

In one embodiment, the translating component 43 includes a linear guide 43b suitable to control the translational motion along the sliding direction 43a that is substantially parallel to the direction 20a. The translating component 43 may include a carriage 43c suitable to slide along the linear guide 43b. In one embodiment, the linear guide 43b is motorized. It has been contemplated that any suitable mechanism can be used to move the gantry 30, either manually or mechanically/automatically.

Referring to the example of FIG. 4, one embodiment of the system includes a rotation device 44 having a first plate 44b that is integrally attached to the carriage 43c. The rotation device 44 may also include a second plate 44c integrally attached to the gantry. In addition, the rotation device 44 may include a rotation component (not shown) that has pins, bearings, or other known mechanical elements suitable to permit the second plate 44c, and thereby the gantry 30, to rotate about the axis of rotation 44a, in relation to the first plate 44b, and therefore to the rest of the radiological imaging system 1. The rotation device 44 also has a control lever 44d, suitable to be held by an operator to control the rotation of the gantry 30 about the axis 44a. A handle or any other type of grip may be used to control the rotation of the gantry 30 about the axis 44a.

In one embodiment, the rotation component and the control lever 44d permit the gantry 30 to be disposed in at least two configurations. One possible configuration is a working configuration where the gantry 30 is substantially perpendicular to the main direction 20a. Another possible configuration is a rest configuration where the gantry 30 is substantially parallel to the main direction 20a. The rotation component and control lever may also permit the gantry to be in a variety of other positions and angles relative to the bed 20.

As shown in the examples provided in figures, the bed 20 is attached to the load-bearing structure 40. In one embodiment, the bed 20 is attached to the two columns 42 of the radiological imaging system 1. As best shown in the embodiment displayed in FIGS. 2a and 2b, the bed 20 has a substantially concave support surface to internally house at least a portion of a patient and, in particular, at least the portion to be analyzed portion of the patient. In one embodiment, the bed 20 has at least two separate bodies 21a and 21b, each of which defines a portion of the support surface. The bed 20 also includes a hinge 22 suitable to retain the separate bodies 21a and 21b allowing the two separate bodies to rotate about an axis of rotation and thereby vary the concavity of the concave support surface. In other embodiment, the bed may not include any hinge. In one embodiment, the separate bodies 21a and 21b have plates or other similar elements defining substantially flat portions that are reciprocally inclined by an angle of aperture α that is not greater than 180°. In certain embodiments, the angle of aperture α is variable between 180° and 45°. In other embodiments, the angle of aperture α is variable between 150° and 90°. In another embodiment, the inclination of the separate bodies 20a and 21b can be achieved without manually or automatically by a motor control.

In the above-described embodiment, the hinge 22 of the bed 20 permits the separate bodies 21a and 21b to rotate about an axis of rotation that is substantially parallel to the main direction 20a. In one embodiment, the hinge 22 is an elastic hinge that is suitable to permit the rotation of the separate bodies by elastic deformation thereof.

The hinge 22 may have one or more strips (e.g., only one strip) positioned between the separate bodies 21a and 21b and suitably characterized by a thickness that is thinner than the thickness of the separate bodies 21a and 21b. In certain embodiments, the thickness of the strips may vary and may even be thicker than the separate bodies. When the operator decides to vary the aperture angle α, a force is applied to elastically deform the hinge 22 into a desired position.

Alternatively to the separate bodies 21a and 21b and the hinge 22, the support surface for the patient is made by a structure of canvas, microfiber or other material that is deformable when the patient is disposed on the bed 20 allowing the support surface to become substantially concave due to the weight of the patient. In this embodiment, no hinge is required, however, a hinge may be included to help shape the support surface for the patient.

In one embodiment, the bed 20 further includes two support profiles 23 positioned laterally to the separate bodies 21a and 21b or the structure of canvas. The support profiles 23 are made of the same material of the separate bodies 21a and 21a, in one embodiment. The bed 20 may include at least one hook 24 (FIG. 1) suitable to permit the separate bodies 21a and 21b or the structure of canvas to be fixed to the support profiles 23. Other means, such as Velcro, screws, snaps, ties, or other fastening devices, may be used to fix the separate bodies or canvas to the support profiles.

In another embodiment, the bed 20 or, at least the separate bodies 21a and 21b and the hinge 22 are made from a radio-transparent material that is transparent to X-rays. Specifically, the separate bodies 21 and the hinge 22 are made from a material having reduced Hounsfield units (HU) such as, for instance, a composite material with a polymer matrix and fiber reinforcement, yet more specifically, in carbon fiber or aramid or glass fiber and matrix in epoxy resin or the like. In yet another embodiment, the bed 20 is removably attached to the load-bearing structure 40 to permit the bed 20 to be fixed firmly to the structure and then to be released and moved away from the rest of the radiological imaging system 1.

By way of example, the radiological imaging system 1 includes at least one retaining apparatus 50 to removably attach the bed to the load-bearing structure 40. In another example, the system may include an adjustment mechanism 60 to adjust the height of the bed 20 from the floor 1a. The radiological imaging system 1 may have two retaining apparatuses 50, each of which is positioned between a column 42 and the bed 20. Only one retaining apparatus may be used as well. In the embodiment shown in FIGS. 2a and 2b, each retaining apparatus 50 is used to fix the bed 20 to the structure 40 with a quick release coupling and, in particular a snap-fit attachment. In other embodiments, the retaining apparatus 50 may include other methods for fixing the bed to the structure, such as using a peg and hole, hooks, ties, or the like.

Figure 2B:
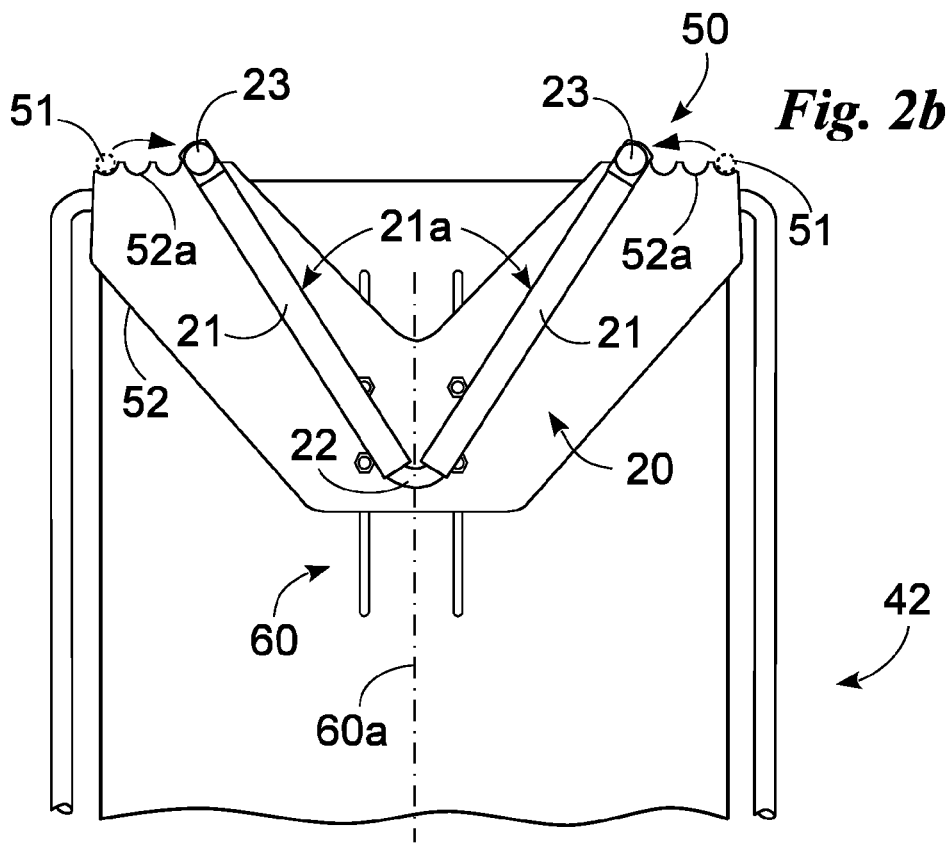
Figure 3:
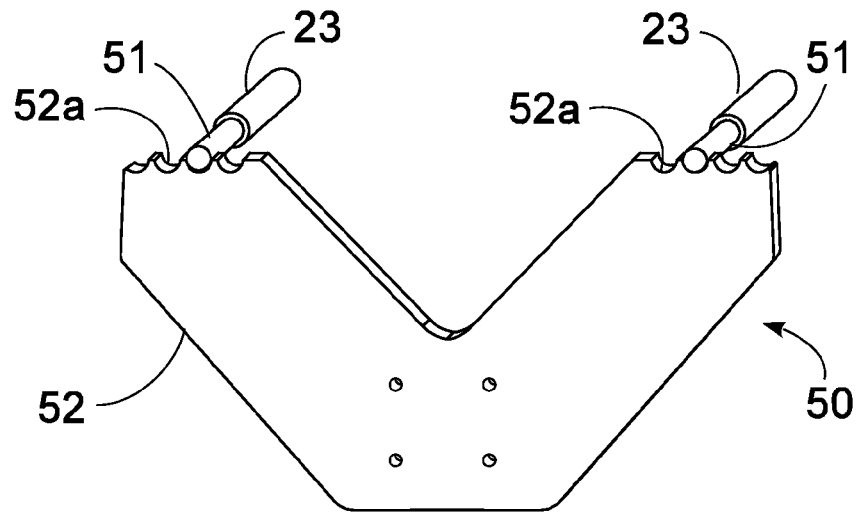
FIG. 3 shows a portion of the radiological imaging system of FIG. 1.

Still referring to the embodiment of FIGS. 2a and 2b, each retaining apparatus 50 has at least one pin 51 projecting from the bed 20 and, in particular from the support profiles 23. In this embodiment, there is at least one seat 52a suitable to house the pin 51 fixing the bed 20 to the load-bearing structure 40. Specifically, each retaining apparatus 50 has two pins 51 integrally attached to the bed 20. Further, there is at least one plate 52 attached to the column 42 and defining, for each pin 51, a plurality of seats 52a suitable to fix the bed 20 to the column 41 independently of the angle of aperture α. The number of seats may vary depending to vary the number of desired positions for the bed.

In some embodiments, the retaining apparatus 50 may include at least one actuator (not shown in the figures) that is configured to move the plate 52 and, therefore, the bed 20 along a direction substantially parallel to the ground 1a, and, preferably, substantially perpendicular to the main direction 20a and to move the bed 20 while maintaining the main direction 20a substantially parallel to the direction of development of the gantry 30. The actuator may be equipped with one or more limit switches to avoid collisions of the bed 20 against the gantry 30.

Additionally, the retaining apparatus 50 may include two plates 52 and two actuators to move independently the plates 20 by varying the angle of aperture α when the bed 20 is connected to the structure 40. Between each plate 52 and the column 42, the radiological imaging system 1 is provided with an adjustment mechanism 60. According to one embodiment, the adjustment mechanism 60 has a linear actuator or similar means suitable to move the plate 52 and, consequently the bed 20 in a direction of translation 60a substantially perpendicular to the main direction 20a and, specifically, substantially perpendicular to the floor 1a. The adjustment mechanism 60 may also allow movement of the bed 20 manually.

By way of example only, and not by way of limitation, a method of using the radiological imaging system will be described. In one embodiment, the bed 20 may be detached from the radiological imaging system 1 when the radiological imaging system 1 is in the rest configuration, that is, with the gantry 30 substantially parallel to the direction 20a. At the moment of use, the operator rotates the gantry 30 about the axis of rotation 44a using the control lever 44d so that the radiological imaging system 1 moves into the working configuration where the gantry 30 is substantially perpendicular to the main direction 20a.

After placing the radiological imaging system 1 in the working configuration, the operator elastically deforms the hinge 22 by modifying the angle of aperture α and consequently adapting the concavity of the support surface of the bed 20 to the requirements of the patient. At this point, the operator places the patient on the bed 20. The patient is pushed into the middle of the concavity of the bed 20. In particular, owing to the concavity of the bed 20, and partially to the effect of gravity, the patient is positioned substantially in the middle of the separate bodies 21a and 21b and is blocked in such a position, preventing any unwanted movements by the patient. In this embodiment, no straps are required to restrain the patient. After placing the patient on the bed 20, the operator raises the bed 20, inserts the bed 20 at least partially in the analysis zone 30a, and fixes the bed 20 to the load-bearing structure 40. The bed may be removably attached to the load-bearing structure 40 to permit the bed 20 to be fixed firmly to the structure and then to be released and moved away from the rest of the radiological imaging system 1. In one embodiment the operator fixes the bed 20 to the columns 42 inserting the pins 51 into the seats 52a and, using the adjustment mechanism 60, translates the bed 20 vertically to place the portion of the patient to be analyzed in the correct position. At this point, using the control unit, the operator controls the translation of the gantry 30 in the sliding direction 43a until the gantry 30 reaches the analysis zone and performs the radiological imaging of the intended portion of the patient.

When the radiological imaging procedure is complete, should the operator deem it necessary to perform a different analysis, the operator releases the bed 20 from the load-bearing structure and, without removing the patient, places the bed 20 on the radiological imaging system 1 and performs a second radiological imaging procedure or alternatively, places the bed 20 on an operating table to perform an operation or on a stretcher to facilitate the movement of the patient. In addition, once the bed 20 has been removed from the radiological imaging system 1, the operator, using the rotation device 44, rotates the gantry 30 by means of the control lever, returning the gantry 30 to the rest configuration.

In view of the foregoing description, it can be appreciated that the radiological imaging system 1, by virtue of the concavity of the bed 20, does not need cushions or other similar blocking means normally used to optimally position a patient, which therefore permits improved imaging owing to the absence of such elements that constitute thicknesses detected during the analysis and cause imaging disturbance. The concavity of the bed 20 avoids the use of cushions or other similar blocking means and makes positioning the patient easier on the bed 20. In particular, the concave shape reduces, if not eliminating entirely, the use of belts, straps and other similar restraints that may prevent a passage of X-rays and therefore the analysis of a portion that is adjacent to such restraints. In fact, by virtue of the concavity of the bed 20, the patient is pushed by the force of gravity against the center of the concavity, thereby preventing the patient from moving and causing poor quality radiological images.

Furthermore, the hinge 22 permits the variation of the angle of aperture α to allow the operator to adapt the concavity of the bed 20 to the needs and size of the patient. In addition, the separate bodies 21a and 21b, the hinge 22, and the entire bed 20 are made of a composite fiber material with a polymer matrix or a radiolucent/radio-transparent material that is transparent to X-rays, thus does not consequently appear in the radiological imaging.

Moreover, the retaining apparatus 50 permits the release of the bed 20 from the structure 40, therefore the patient can be moved without having to be lifted from the bed 20. As a result, the possibility of moving the patient on the bed 20 makes it possible to move the patient around and thereby perform several analyses and carry out operations in safety. Consequently, the time needed to perform the aforementioned maneuvers can be reduced.

Furthermore, by virtue of the possibility of removing the bed 20 and rotating the gantry 30, it is possible to place the radiological imaging system 1 in the rest configuration in which the gantry positioned parallel to the main direction 20a. In the rest configuration, the radiological imaging system 1 has reduced dimensions and is therefore easy to maneuver compared to the prior art devices.

Variations may be made to the embodiments described herein without departing from the scope of the present disclosure. All the elements described and claimed may be replaced by equivalent elements and the parts, materials, shapes and dimensions may be chosen as needed.

What is claimed:

1. A radiological imaging system comprising:
   a bed extending along a main direction and having a support surface for a patient, and the support surface is substantially concave to permit the bed to contain at least a portion of the patient;
   a source suitable to emit radiation; and
   at least one detector suitable to receive the radiation and to be positioned substantially on the opposite side to the source in relation to the bed.

2. The radiological imaging system as claimed in claim 1, wherein the bed comprises at least two separate bodies, defining a portion of the support surface; and wherein the two separate bodies are reciprocally inclined by an angle of aperture ($\alpha$) substantially between 180° and 45°.

3. The radiological imaging system as claimed in claim 2, wherein the angle of aperture ($\alpha$) is substantially between 150° and 90°.

4. The radiological imaging system as claimed in claim 2, wherein the bed includes a hinge suitable to retain the separate bodies allowing the separate bodies to rotate about an axis of rotation.

5. The radiological imaging system as claimed in claim 4, wherein the hinge is an elastic hinge.

6. The radiological imaging system as claimed in claim 4, wherein the axis of rotation is substantially parallel to the main direction.

7. The radiological imaging system as claimed in claim 1, wherein the bed is made of a radio-transparent material.

8. The radiological imaging system as claimed in claim 7, wherein the radio-transparent material is carbon fiber, a composite material with a polymer matrix and a carbon fiber, aramid, or a glass fiber.

9. The radiological imaging system as claimed in claim 1, further comprising a load-bearing structure.

10. The radiological imaging system as claimed in claim 9, further comprising at least one retaining apparatus suitable to removably fix the load-bearing structure to the bed.

11. The radiological imaging system as claimed in claim 10, wherein the at least one retaining apparatus is suitable to fix the load-bearing structure to the bed using a snap-fit attachment.

12. A method of obtaining radiological images of a patient, the method comprising:
    placing the patient on a bed removably attached to a radiological imaging device, the bed extending along a main direction and having a support surface for a patient, and the support surface is substantially concave to permit the bed to contain at least a portion of the patient;
    emitting radiation from a source of the radiological imaging device to a portion of the patient confined in the bed; and
    receiving the radiation using at least one detector, wherein the at least one detector is positioned substantially on an opposite side to the source in relation to the bed.

13. The method of claim 12, wherein the bed comprises at least two separate bodies, defining a portion of the support surface, and wherein the two separate bodies are reciprocally inclined by an angle of aperture.

14. The method of claim 13, further comprising rotating the separate bodies of the bed with a hinge about an axis of rotation.

15. The method of claim 14, wherein the hinge is an elastic hinge.

16. The method of claim 14, wherein the axis of rotation is substantially parallel to an extending direction of the bed.

17. The method of claim 12, wherein the bed is made of a radio-transparent material.

18. The method of claim 17, wherein the radio-transparent material is carbon fiber.

19. The method of claim 12, further comprising attaching the bed to the radiological imaging system with at least one retaining apparatus.

20. The method of claim 19, wherein attaching the bed to the radiological imaging system with a snap-fit attachment.

21. A bed for adjusting a position of a patient, the bed comprising:
    a support surface for the patient, the support surface being substantially concave to permit the bed to contain at least a portion of the patient; and
    at least two separate bodies, defining a portion of the support surface; and wherein the two separate bodies are reciprocally inclined by an angle of aperture ($\alpha$).

22. The bed of claim 21, further comprising a hinge suitable to retain the separate bodies allowing the separate bodies to rotate about an axis of rotation.

23. The bed of claim 21, wherein the angle of aperture ($\alpha$) is substantially between 180° and 45°.

24. The bed of claim 21, wherein the angle of aperture ($\alpha$) is substantially between 150° and 90°.

25. The bed of claim 21, wherein the axis of rotation is substantially parallel to the main direction.

26. The bed of claim 21, wherein the bed is made of a radio-transparent material.

27. The bed of claim 26, wherein the radio-transparent material is carbon fiber.

* * * * *